(12) United States Patent
Carballido Herrera et al.

(10) Patent No.: US 7,740,843 B2
(45) Date of Patent: Jun. 22, 2010

(54) HUMAN MONOCLONAL ANTIBODIES AGAINST HUMAN IL-4

(75) Inventors: José M. Carballido Herrera, Perchtoldsdorf (AT); Jan E. De Vries, Vienna (AT); Christoph Schwaerzler, Vienna (AT)

(73) Assignee: Novartis AG, Basel (CH)

( * ) Notice: Subject to any disclaimer, the term of this patent is extended or adjusted under 35 U.S.C. 154(b) by 189 days.

(21) Appl. No.: 11/632,939

(22) PCT Filed: Aug. 2, 2005

(86) PCT No.: PCT/EP2005/008361

§ 371 (c)(1), (2), (4) Date: May 15, 2007

(87) PCT Pub. No.: WO2006/013087

PCT Pub. Date: Feb. 9, 2006

(65) Prior Publication Data

US 2008/0241160 A1    Oct. 2, 2008

(30) Foreign Application Priority Data

| Aug. 3, 2004 | (GB) | ................................. | 0417301.9 |
| Aug. 3, 2004 | (GB) | ................................. | 0417302.7 |
| Aug. 3, 2004 | (GB) | ................................. | 0417303.5 |
| Aug. 3, 2004 | (GB) | ................................. | 0417304.3 |
| Aug. 3, 2004 | (GB) | ................................. | 0417305.0 |
| Aug. 3, 2004 | (GB) | ................................. | 0417306.8 |

(51) Int. Cl.
*C07K 16/24* (2006.01)
*A61K 39/395* (2006.01)

(52) U.S. Cl. .................. 424/130.1; 530/387.1

(58) Field of Classification Search .............. None
See application file for complete search history.

(56) References Cited

U.S. PATENT DOCUMENTS

| 5,705,154 A | 1/1998 | Dalie et al. ............. 424/130.1 |
| 5,914,110 A * | 6/1999 | Holmes et al. ........... 424/133.1 |
| 2002/0002132 A1 | 1/2002 | Pluenneke ................. 514/12 |

FOREIGN PATENT DOCUMENTS

| WO | 93/17106 A1 | 9/1993 |
| WO | 2004/058797 A2 | 7/2004 |

OTHER PUBLICATIONS

Yau, et al., "Emerging trends in the synthesis and improvement of hapten-specific recombinant antibodies," Biotechnology Advances 21:599-637 (2003).

* cited by examiner

*Primary Examiner*—Marianne P Allen
(74) *Attorney, Agent, or Firm*—Karen A. Lacourse

(57) ABSTRACT

Antibodies which are specific for human interleukin-4 and their use in the treatment of IL-4 and/or IgE mediated diseases.

4 Claims, No Drawings

SEQUENCE LISTING

<160> NUMBER OF SEQ ID NOS: 79

<210> SEQ ID NO 1
<211> LENGTH: 120
<212> TYPE: PRT
<213> ORGANISM: Homo Sapiens

<400> SEQUENCE: 1

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Thr Phe Ile Trp Asp Asp Gly Ser Phe Lys Tyr Tyr Ala Glu Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ser Trp Ser Pro Asp Ile Phe Asp Ile Trp Gly Gln
            100                 105                 110

Gly Thr Met Val Thr Val Ser Ser
        115                 120
```

<210> SEQ ID NO 2
<211> LENGTH: 109
<212> TYPE: PRT
<213> ORGANISM: Homo Sapiens

<400> SEQUENCE: 2

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Arg Ala
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Ile
                85                  90                  95

Thr Phe Gly Gln Gly Thr Arg Leu Glu Ile Lys Arg Thr
            100                 105
```

<210> SEQ ID NO 3
<211> LENGTH: 139
<212> TYPE: PRT
<213> ORGANISM: Homo Sapiens

<400> SEQUENCE: 3

Met Glu Phe Gly Leu Asn Trp Val Phe Leu Val Ala Leu Phe Arg Gly
1               5                   10                  15

Val His Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Ala Met His Trp Val Arg Gln Ala Pro Gly Lys Gly Leu
    50                  55                  60

Glu Trp Val Thr Phe Ile Trp Asp Asp Gly Ser Phe Lys Tyr Tyr Ala
65                  70                  75                  80

Glu Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Glu Gly Ser Trp Ser Pro Asp Ile Phe Asp Ile
        115                 120                 125

Trp Gly Gln Gly Thr Met Val Thr Val Ser Ser
    130                 135

<210> SEQ ID NO 4
<211> LENGTH: 131
<212> TYPE: PRT
<213> ORGANISM: Homo Sapiens

<400> SEQUENCE: 4

Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Arg Ala Leu Ala Trp Tyr Gln Gln Lys Pro Gly Lys
    50                  55                  60

Ala Pro Lys Leu Leu Ile Tyr Asp Ala Ser Ser Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Tyr Pro Ile Thr Phe Gly Gln Gly Thr Arg Leu Glu Ile
        115                 120                 125

Lys Arg Thr
    130

<210> SEQ ID NO 5
<211> LENGTH: 360
<212> TYPE: DNA
<213> ORGANISM: Homo Sapiens

<400> SEQUENCE: 5

```
caggtgcagc tggtggagtc tgggggaggc gtggtccagc ctgggaggtc cctgagactc      60
tcctgtgcag cgtctggatt caccttcagt agctatgcca tgcactgggt ccgccaggct     120
ccaggcaagg ggctggagtg ggtgacattt atatgggatg atggaagttt taaatattat     180
gcagagtccg tgaagggccg attcaccatc tccagagaca attccaagaa cacgctgtat     240
ttgcaaatga acagcctgag agccgaagac acggctgtgt attactgtgc gagagagggc     300
agctggtctc ctgatatatt tgatatctgg ggccaaggga caatggtcac cgtctcttca     360
```

<210> SEQ ID NO 6
<211> LENGTH: 327
<212> TYPE: DNA
<213> ORGANISM: Homo Sapiens

<400> SEQUENCE: 6

```
gccatccagt tgacccagtc tccatcctcc ctgtctgcat ctgtaggaga cagagtcacc      60
atcacttgcc gggcaagtca gggcattagc agagctttag cctggtatca gcagaaacca     120
gggaaagctc ctaagctcct gatctatgat gcctccagtt tggaaagtgg ggtcccatca     180
aggttcagcg gcagtggatc tgggacagat ttcactctca ccatcagcag cctgcagcct     240
gaagattttg caacttatta ctgtcaacag tttaatagtt accccatcac cttcggccaa     300
gggacacgac tggagattaa acgaact                                          327
```

<210> SEQ ID NO 7
<211> LENGTH: 417
<212> TYPE: DNA
<213> ORGANISM: Homo Sapiens

<400> SEQUENCE: 7

```
atggagtttg ggctgaactg ggttttcctc gttgctcttt tcagaggtgt ccactgtcag      60
gtgcagctgg tggagtctgg gggaggcgtg gtccagcctg ggaggtccct gagactctcc     120
tgtgcagcgt ctggattcac cttcagtagc tatgccatgc actgggtccg ccaggctcca     180
ggcaaggggc tggagtgggt gacatttata tgggatgatg gaagttttaa atattatgca     240
gagtccgtga agggccgatt caccatctcc agagacaatt ccaagaacac gctgtatttg     300
caaatgaaca gcctgagagc cgaagacacg gctgtgtatt actgtgcgag agagggcagc     360
tggtctcctg atatatttga tatctggggc caagggacaa tggtcaccgt ctcttca       417
```

<210> SEQ ID NO 8
<211> LENGTH: 393
<212> TYPE: DNA
<213> ORGANISM: Homo Sapiens

<400> SEQUENCE: 8

```
atggacatga gggtccccgc tcagctcctg gggcttctgc tgctctggct cccaggtgcc      60
agatgtgcca tccagttgac ccagtctcca tcctccctgt ctgcatctgt aggagacaga     120
gtcaccatca cttgccgggc aagtcagggc attagcagag ctttagcctg gtatcagcag     180
aaaccaggga aagctcctaa gctcctgatc tatgatgcct ccagtttgga aagtggggtc     240
ccatcaaggt tcagcggcag tggatctggg acagatttca ctctcaccat cagcagcctg     300
cagcctgaag attttgcaac ttattactgt caacagttta atagttaccc catcaccttc     360
ggccaaggga cacgactgga gattaaacga act                                   393
```

<210> SEQ ID NO 9
<211> LENGTH: 120

```
<212> TYPE: PRT
<213> ORGANISM: Homo Sapiens

<400> SEQUENCE: 9

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Leu Ser Ser Phe
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Glu Tyr Tyr Ala Asp Ser Val
    50                  55                  60

Lys Gly Arg Phe Thr Thr Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ser Trp Ser Pro Asp Ile Phe Asp Ile Trp Gly Gln
            100                 105                 110

Gly Thr Met Val Thr Val Ser Ser
        115                 120

<210> SEQ ID NO 10
<211> LENGTH: 109
<212> TYPE: PRT
<213> ORGANISM: Homo Sapiens

<400> SEQUENCE: 10

Ala Ile Gln Leu Thr Gln Ser Pro Ser Ser Leu Ser Ala Ser Val Gly
1               5                   10                  15

Asp Arg Val Thr Ile Thr Cys Arg Thr Ser Gln Gly Ile Arg Ser Ala
            20                  25                  30

Leu Ala Trp Tyr Gln Gln Asn Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Val
                85                  90                  95

Thr Phe Gly Gln Gly Thr Arg Leu Glu Ile Lys Arg Thr
            100                 105

<210> SEQ ID NO 11
<211> LENGTH: 139
<212> TYPE: PRT
<213> ORGANISM: Homo Sapiens

<400> SEQUENCE: 11

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Val Val Gln
            20                  25                  30

Pro Gly Arg Ser Leu Arg Leu Ser Cys Ala Ala Ser Gly Phe Thr Leu
        35                  40                  45

Ser Ser Phe Gly Met His Trp Val Arg Gln Ala Pro Gly Lys Gly Leu
    50                  55                  60

Glu Trp Val Ala Val Ile Trp Tyr Asp Gly Ser Asn Glu Tyr Tyr Ala
```

```
                65                  70                  75                  80
Asp Ser Val Lys Gly Arg Phe Thr Thr Ser Arg Asp Asn Ser Lys Asn
                    85                  90                  95

Thr Leu Tyr Leu Gln Met Asn Ser Leu Arg Ala Glu Asp Thr Ala Val
            100                 105                 110

Tyr Tyr Cys Ala Arg Glu Gly Ser Trp Ser Pro Asp Ile Phe Asp Ile
        115                 120                 125

Trp Gly Gln Gly Thr Met Val Thr Val Ser Ser
    130                 135

<210> SEQ ID NO 12
<211> LENGTH: 131
<212> TYPE: PRT
<213> ORGANISM: Homo Sapiens

<400> SEQUENCE: 12

Met Asp Met Arg Val Pro Ala Gln Leu Gly Leu Leu Leu Leu Trp
1               5                   10                  15

Leu Pro Gly Ala Arg Cys Ala Ile Gln Leu Thr Gln Ser Pro Ser
            20                  25                  30

Leu Ser Ala Ser Val Gly Asp Arg Val Thr Ile Thr Cys Arg Thr Ser
        35                  40                  45

Gln Gly Ile Arg Ser Ala Leu Ala Trp Tyr Gln Asn Pro Gly Lys
    50                  55                  60

Ala Pro Lys Leu Leu Ile Tyr Asp Ala Ser Ser Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Tyr Pro Val Thr Phe Gly Gln Gly Thr Arg Leu Glu Ile
        115                 120                 125

Lys Arg Thr
    130

<210> SEQ ID NO 13
<211> LENGTH: 360
<212> TYPE: DNA
<213> ORGANISM: Homo Sapiens

<400> SEQUENCE: 13
caggtgcaac tggtggagtc ggggggaggc gtggtccagc ctggagggtc cctgagactc      60
tcctgtgcag cgtctggatt caccttaagt agctttggca tgcactgggt ccgccaggct     120
ccaggcaagg ggctggagtg ggtggcagtt atatggtatg atggaagtaa tgaatactat     180
gcagactccg tgaagggccg attcaccacc tccagagaca attccaagaa cacgctgtat     240
ctgcaaatga acagcctgag agccgaggac acggctgtgt attactgtgc gagagagggc     300
agctggtctc ctgatatttt tgatatctgg ggccaaggga caatggtcac cgtctcttca     360

<210> SEQ ID NO 14
<211> LENGTH: 327
<212> TYPE: DNA
<213> ORGANISM: Homo Sapiens

<400> SEQUENCE: 14
gccatccagt tgacccagtc tccatcctcc ctgtctgcat ctgtaggaga cagagtcacc      60
```

-continued

| | |
|---|---|
| atcacttgcc ggacaagtca gggcattcgc agtgctttag cctggtatca gcagaacccc | 120 |
| gggaaagctc ctaagctcct gatctatgat gcctccagtt tggaaagtgg ggtcccatca | 180 |
| aggttcagcg gcagtggatc tgggacagat ttcactctca ccatcagcag cctgcagcct | 240 |
| gaagattttg caacttatta ctgtcaacag tttaatagtt accccgtcac cttcggccaa | 300 |
| gggacacgac tggagattaa acgaact | 327 |

<210> SEQ ID NO 15
<211> LENGTH: 417
<212> TYPE: DNA
<213> ORGANISM: Homo Sapiens

<400> SEQUENCE: 15

| | |
|---|---|
| atggagtttg gctgagctg ggttttcctc gttgctcttt taagaggtgt ccagtgtcag | 60 |
| gtgcaactgg tggagtcggg gggaggcgtg gtccagcctg gaggtccct gagactctcc | 120 |
| tgtgcagcgt ctggattcac cttaagtagc tttggcatgc actgggtccg ccaggctcca | 180 |
| ggcaagggc tggagtgggt ggcagttata tggtatgatg aagtaatga atactatgca | 240 |
| gactccgtga agggccgatt caccacctcc agagacaatt ccaagaacac gctgtatctg | 300 |
| caaatgaaca gcctgagagc cgaggacacg gctgtgtatt actgtgcgag agagggcagc | 360 |
| tggtctcctg atattttga tatctggggc caagggacaa tggtcaccgt ctcttca | 417 |

<210> SEQ ID NO 16
<211> LENGTH: 393
<212> TYPE: DNA
<213> ORGANISM: Homo Sapiens

<400> SEQUENCE: 16

| | |
|---|---|
| atggacatga gggtccccgc tcagctcctg gggcttctgc tgctctggct cccaggtgcc | 60 |
| agatgtgcca tccagttgac ccagtctcca tcctccctgt ctgcatctgt aggagacaga | 120 |
| gtcaccatca cttgccggac aagtcagggc attcgcagtg ctttagcctg gtatcagcag | 180 |
| aaccccggga agctcctaa gctcctgatc tatgatgcct ccagtttgga aagtggggtc | 240 |
| ccatcaaggt tcagcggcag tggatctggg acagatttca ctctcaccat cagcagcctg | 300 |
| cagcctgaag attttgcaac ttattactgt caacagttta atagttaccc cgtcaccttc | 360 |
| ggccaaggga cacgactgga gattaaacga act | 393 |

<210> SEQ ID NO 17
<211> LENGTH: 120
<212> TYPE: PRT
<213> ORGANISM: Homo Sapiens

<400> SEQUENCE: 17

Gln Val Gln Leu Val Glu Ser Gly Gly Gly Met Val Gln Pro Gly Arg
1               5                   10                  15

Ser Leu Arg Leu Ser Cys Ala Ala Ser Gly Phe Thr Leu Ser Ser Tyr
            20                  25                  30

Gly Met His Trp Val Arg Gln Ala Pro Gly Lys Gly Leu Glu Trp Val
        35                  40                  45

Thr Val Ile Trp Tyr Asp Gly Asn Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

```
Ala Arg Glu Gly Ser Trp Ser Pro Asp Ile Phe Asp Ile Trp Gly Gln
                100                 105                 110
Gly Thr Met Val Thr Val Ser Ser
        115                 120

<210> SEQ ID NO 18
<211> LENGTH: 109
<212> TYPE: PRT
<213> ORGANISM: Homo Sapiens

<400> SEQUENCE: 18

Ala Ile Gln Leu Thr Gln Ser Pro Ser Ser Leu Ser Ala Ser Val Gly
1               5                   10                  15
Asp Arg Val Thr Ile Thr Cys Arg Ala Ser Gln Gly Ile Ser Ser Tyr
            20                  25                  30
Leu Ala Trp Tyr Gln Gln Lys Pro Gly Lys Ala Pro Lys Leu Leu Ile
        35                  40                  45
Tyr Asp Ala Ser Ser Leu Glu Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Phe Asn Ser Tyr Pro Ile
                85                  90                  95
Thr Phe Gly Gln Gly Thr Arg Leu Glu Ile Lys Arg Thr
            100                 105

<210> SEQ ID NO 19
<211> LENGTH: 139
<212> TYPE: PRT
<213> ORGANISM: Homo Sapiens

<400> SEQUENCE: 19

Met Glu Phe Gly Leu Ser Trp Val Phe Leu Val Ala Leu Leu Arg Gly
1               5                   10                  15
Val Gln Cys Gln Val Gln Leu Val Glu Ser Gly Gly Gly Met Val Gln
            20                  25                  30
Pro Gly Arg Ser Leu Arg Leu Ser Cys Ala Ala Ser Gly Phe Thr Leu
        35                  40                  45
Ser Ser Tyr Gly Met His Trp Val Arg Gln Ala Pro Gly Lys Gly Leu
    50                  55                  60
Glu Trp Val Thr Val Ile Trp Tyr Asp Gly Asn Asn Gln Tyr Tyr Ala
65                  70                  75                  80
Asp Ser Val Lys Gly Arg Phe Thr Ile Ser Arg Asp Asn Ser Lys Asn
                85                  90                  95
Thr Leu Tyr Leu Gln Met Asn Ser Leu Arg Ala Glu Asp Thr Ala Val
            100                 105                 110
Tyr Tyr Cys Ala Arg Glu Gly Ser Trp Ser Pro Asp Ile Phe Asp Ile
        115                 120                 125
Trp Gly Gln Gly Thr Met Val Thr Val Ser Ser
    130                 135

<210> SEQ ID NO 20
<211> LENGTH: 131
<212> TYPE: PRT
<213> ORGANISM: Homo Sapiens

<400> SEQUENCE: 20
```

```
Met Asp Met Arg Val Pro Ala Gln Leu Leu Gly Leu Leu Leu Trp
1               5                   10                  15

Leu Pro Gly Ala Arg Cys Ala Ile Gln Leu Thr Gln Ser Pro Ser
                20              25                  30

Leu Ser Ala Ser Val Gly Asp Arg Val Thr Ile Thr Cys Arg Ala Ser
            35              40                  45

Gln Gly Ile Ser Ser Tyr Leu Ala Trp Tyr Gln Gln Lys Pro Gly Lys
        50              55                  60

Ala Pro Lys Leu Leu Ile Tyr Asp Ala Ser Ser Leu Glu Ser Gly Val
65              70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
                100                 105                 110

Phe Asn Ser Tyr Pro Ile Thr Phe Gly Gln Gly Thr Arg Leu Glu Ile
            115                 120                 125

Lys Arg Thr
        130
```

<210> SEQ ID NO 21
<211> LENGTH: 360
<212> TYPE: DNA
<213> ORGANISM: Homo Sapiens

<400> SEQUENCE: 21

```
caggtgcagc tggtggagtc tgggggaggc atggtccagc ctgggaggtc cctgagactc    60
tcctgtgcag cgtctggatt caccctcagt agctatggca tgcactgggt ccgccaggct   120
ccaggcaagg ggctggagtg ggtgacagtt atatggtatg atggaaataa tcaatactat   180
gcagactccg tgaagggccg attcaccatc tccagagaca attccaagaa cacgctgtat   240
ctgcaaatga acagcctgag agccgaggac acggctgtat attactgtgc gagagagggc   300
agctggtctc ctgatatttt tgatatctgg ggccaaggga caatggtcac cgtctcttca   360
```

<210> SEQ ID NO 22
<211> LENGTH: 327
<212> TYPE: DNA
<213> ORGANISM: Homo Sapiens

<400> SEQUENCE: 22

```
gccatccagt tgacccagtc tccatcctcc ctgtctgcat ctgtaggaga cagagtcacc    60
atcacttgcc gggcaagtca gggcattagc agttatttag cctggtatca gcagaaacca   120
gggaaagctc ctaagctcct gatctatgat gcctccagtt tggaaagtgg ggtcccatca   180
aggttcagcg gcagtggatc tgggacagat ttcactctca ccatcagcag cctgcagcct   240
gaagattttg caacttatta ctgtcaacag tttaatagtt accccatcac cttcggccaa   300
gggacacgac tggagattaa acgaact                                       327
```

<210> SEQ ID NO 23
<211> LENGTH: 417
<212> TYPE: DNA
<213> ORGANISM: Homo Sapiens

<400> SEQUENCE: 23

```
atggagtttg ggctgagctg gttttcctc gttgctctttt taagaggtgt ccagtgtcag    60
gtgcagctgg tggagtctgg gggaggcatg gtccagcctg gaggtccct gagactctcc   120
```

-continued

```
tgtgcagcgt ctggattcac cctcagtagc tatggcatgc actgggtccg ccaggctcca    180 ggcaagggc tggagtgggt gacagttata tggtatgatg gaaataatca atactatgca     240
gactccgtga agggccgatt caccatctcc agagacaatt ccaagaacac gctgtatctg    300
caaatgaaca gcctgagagc cgaggacacg gctgtatatt actgtgcgag agagggcagc    360
tggtctcctg atattttga tatctgggc caagggacaa tggtcaccgt ctcttca         417
```

<210> SEQ ID NO 24
<211> LENGTH: 393
<212> TYPE: DNA
<213> ORGANISM: Homo Sapiens

<400> SEQUENCE: 24

```
atggacatga gggtccccgc tcagctcctg gggcttctgc tgctctggct cccaggtgcc    60
agatgtgcca tccagttgac ccagtctcca tcctccctgt ctgcatctgt aggagacaga    120
gtcaccatca cttgccgggc aagtcagggc attagcagtt atttagcctg gtatcagcag    180
aaaccaggga aagctcctaa gctcctgatc tatgatgcct ccagtttgga aagtggggtc    240
ccatcaaggt tcagcggcag tggatctggg acagatttca ctctcaccat cagcagcctg    300
cagcctgaag attttgcaac ttattactgt caacagttta atagttaccc catcaccttc    360
ggccaaggga cacgactgga gattaaacga act                                 393
```

<210> SEQ ID NO 25
<211> LENGTH: 116
<212> TYPE: PRT
<213> ORGANISM: Homo Sapiens

<400> SEQUENCE: 25

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Ser Tyr
            20                  25                  30

Ala Ile Ser Trp Val Arg Gln Ala Pro Gly Gln Gly Phe Glu Trp Met
        35                  40                  45

Gly Gly Ile Ile Pro Val Ile Gly Thr Val Asn Tyr Glu Glu Arg Phe
    50                  55                  60

Gln Asp Arg Val Thr Ile Thr Ala Asp Asn Ser Thr Ser Thr Ala Tyr
65                  70                  75                  80

Met Glu Leu Thr Ser Leu Arg Ser Glu Asp Thr Ala Val Tyr Phe Cys
                85                  90                  95

Gly Arg Glu Glu Gly Phe Leu Asp Tyr Trp Gly Gln Gly Thr Leu Val
            100                 105                 110

Thr Val Ser Ser
        115

<210> SEQ ID NO 26
<211> LENGTH: 110
<212> TYPE: PRT
<213> ORGANISM: Homo Sapiens

<400> SEQUENCE: 26

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile

```
                35                  40                  45
Tyr Asp Ala Ser Ser Leu Glu Ser Gly Val Pro Ser Arg Phe Ser Gly
     50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Phe Asn Ser Tyr Pro Leu
                 85                  90                  95
Leu Thr Phe Gly Gly Gly Thr Lys Val Glu Ile Lys Arg Thr
            100                 105                 110

<210> SEQ ID NO 27
<211> LENGTH: 135
<212> TYPE: PRT
<213> ORGANISM: Homo Sapiens

<400> SEQUENCE: 27

Met Asp Trp Thr Trp Arg Phe Leu Phe Val Val Ala Ala Ala Thr Gly
1               5                   10                  15
Val Gln Ser Gln Val Gln Leu Val Gln Ser Gly Ala Glu Val Lys Lys
            20                  25                  30
Pro Gly Ser Ser Val Lys Val Ser Cys Lys Ala Ser Gly Asp Thr Phe
         35                  40                  45
Ser Ser Tyr Ala Ile Ser Trp Val Arg Gln Ala Pro Gly Gln Gly Phe
     50                  55                  60
Glu Trp Met Gly Gly Ile Ile Pro Val Ile Gly Thr Val Asn Tyr Glu
65                  70                  75                  80
Glu Arg Phe Gln Asp Arg Val Thr Ile Thr Ala Asp Asn Ser Thr Ser
                 85                  90                  95
Thr Ala Tyr Met Glu Leu Thr Ser Leu Arg Ser Glu Asp Thr Ala Val
            100                 105                 110
Tyr Phe Cys Gly Arg Glu Glu Gly Phe Leu Asp Tyr Trp Gly Gln Gly
         115                 120                 125
Thr Leu Val Thr Val Ser Ser
     130                 135

<210> SEQ ID NO 28
<211> LENGTH: 132
<212> TYPE: PRT
<213> ORGANISM: Homo Sapiens

<400> SEQUENCE: 28

Met Asp Met Arg Val Pro Ala Gln Leu Leu Gly Leu Leu Leu Leu Trp
1               5                   10                  15
Leu Pro Gly Ala Arg Cys Ala Ile Gln Leu Thr Gln Ser Pro Ser Ser
            20                  25                  30
Leu Ser Ala Ser Val Gly Asp Arg Val Thr Ile Thr Cys Arg Ala Ser
         35                  40                  45
Gln Gly Ile Ser Ser Ala Leu Ala Trp Tyr Gln Gln Lys Pro Gly Lys
     50                  55                  60
Ala Pro Lys Leu Leu Ile Tyr Asp Ala Ser Ser Leu Glu Ser Gly Val
65                  70                  75                  80
Pro Ser Arg Phe Ser Gly Ser Gly Ser Gly Thr Asp Phe Thr Leu Thr
                 85                  90                  95
Ile Ser Ser Leu Gln Pro Glu Asp Phe Ala Thr Tyr Tyr Cys Gln Gln
            100                 105                 110
Phe Asn Ser Tyr Pro Leu Leu Thr Phe Gly Gly Gly Thr Lys Val Glu
```

```
                115                 120                 125
Ile Lys Arg Thr
    130

<210> SEQ ID NO 29
<211> LENGTH: 348
<212> TYPE: DNA
<213> ORGANISM: Homo Sapiens

<400> SEQUENCE: 29
caggtccagc tggtgcagtc tggggctgag gtgaagaagc ctgggtcctc ggtgaaggtc     60
tcctgcaagg cttctggaga caccttcagc agttatgcta tcagttgggt gcgacaggcc    120
cctggacaag gctttgagtg gatgggaggg atcatccctg tcattggtac agtaaattat    180
gaagagagat ccaggacaga gtcacgatt accgcggaca attccacgag cacagcctac    240
atggagttga ctagtctgag atctgaagac acggccgtgt attttgtgg gagagaagag     300 ggcttccttg actattgggg ccagggaacc ctggtcaccg tctcctca                348

<210> SEQ ID NO 30
<211> LENGTH: 396
<212> TYPE: DNA
<213> ORGANISM: Homo Sapiens

<400> SEQUENCE: 30
atggacatga gggtccccgc tcagctcctg gggcttctgc tgctctggct cccaggtgcc     60
agatgtgcca tccagttgac ccagtctcca tcctccctgt ctgcatctgt aggagacaga    120
gtcaccatca cttgccgggc aagtcagggc attagcagtg ctttagcctg gtatcagcag    180
aaaccaggga aagctcctaa gctcctgatc tatgatgcct ccagtttgga aagtggggtc    240
ccatcaaggt tcagcggcag tggatctggg acagatttca ctctcaccat cagcagcctg    300
cagcctgaag attttgcaac ttattactgt caacagttta atagttaccc tcttctcact    360
ttcggcggag ggaccaaggt ggagatcaaa cgtacg                              396

<210> SEQ ID NO 31
<211> LENGTH: 405
<212> TYPE: DNA
<213> ORGANISM: Homo Sapiens

<400> SEQUENCE: 31
atggactgga cctggaggtt cctctttgtg gtggcagcag ctacaggtgt ccagtcccag     60
gtccagctgg tgcagtctgg ggctgaggtg aagaagcctg gtcctcggt gaaggtctcc    120 tgcaaggctt ctggagacac cttcagcagt tatgctatca gttgggtgcg acaggcccct    180
ggacaagggt ttgagtggat gggagggatc atccctgtca ttggtacagt aaattatgaa    240
gagagattcc aggacagagt cacgattacc gcggacaatt ccacgagcac agcctacatg    300
gagttgacta gtctgagatc tgaagacacg gccgtgtatt tttgtgggag agaagagggc    360
ttccttgact attggggcca gggaaccctg gtcaccgtct cctca                   405

<210> SEQ ID NO 32
<211> LENGTH: 396
<212> TYPE: DNA
<213> ORGANISM: Homo Sapiens

<400> SEQUENCE: 32
atggacatga gggtccccgc tcagctcctg gggcttctgc tgctctggct cccaggtgcc     60
```

```
agatgtgcca tccagttgac ccagtctcca tcctccctgt ctgcatctgt aggagacaga    120
gtcaccatca cttgccgggc aagtcagggc attagcagtg ctttagcctg gtatcagcag    180
aaaccaggga agctcctaa gctcctgatc tatgatgcct ccagtttgga aagtggggtc     240
ccatcaaggt tcagcggcag tggatctggg acagatttca ctctcaccat cagcagcctg    300
cagcctgaag attttgcaac ttattactgt caacagttta atagttaccc tcttctcact    360
ttcggcggag ggaccaaggt ggagatcaaa cgtacg                              396
```

<210> SEQ ID NO 33
<211> LENGTH: 121
<212> TYPE: PRT
<213> ORGANISM: Homo Sapiens

<400> SEQUENCE: 33

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Cys Cys
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Asp Ser Ser Gly Ser Phe Tyr Glu Tyr Phe Gln His Trp Gly
            100                 105                 110

Gln Gly Thr Leu Val Thr Val Ser Ser
        115                 120
```

<210> SEQ ID NO 34
<211> LENGTH: 109
<212> TYPE: PRT
<213> ORGANISM: Homo Sapiens

<400> SEQUENCE: 34

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Asn Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys Arg Thr
            100                 105
```

<210> SEQ ID NO 35
<211> LENGTH: 140
<212> TYPE: PRT
<213> ORGANISM: Homo Sapiens

<400> SEQUENCE: 35

| Met | Glu | Phe | Gly | Leu | Ser | Trp | Val | Phe | Leu | Val | Ala | Leu | Leu | Arg | Gly |
|---|---|---|---|---|---|---|---|---|---|---|---|---|---|---|---|
| 1 | | | | 5 | | | | | 10 | | | | | 15 | |

| Val | Gln | Cys | Gln | Val | Gln | Leu | Val | Glu | Ser | Gly | Gly | Gly | Val | Val | Gln |
|---|---|---|---|---|---|---|---|---|---|---|---|---|---|---|---|
| | | | 20 | | | | | 25 | | | | | 30 | | |

| Pro | Gly | Arg | Ser | Leu | Arg | Leu | Ser | Cys | Ala | Ala | Ser | Gly | Phe | Thr | Phe |
|---|---|---|---|---|---|---|---|---|---|---|---|---|---|---|---|
| | | | 35 | | | | | 40 | | | | | 45 | | |

| Ser | Cys | Cys | Gly | Met | His | Trp | Val | Arg | Gln | Ala | Pro | Gly | Lys | Gly | Leu |
|---|---|---|---|---|---|---|---|---|---|---|---|---|---|---|---|
| | 50 | | | | | 55 | | | | | 60 | | | | |

| Glu | Trp | Val | Ala | Val | Ile | Trp | Tyr | Asp | Gly | Ser | Asn | Lys | Tyr | Tyr | Ala |
|---|---|---|---|---|---|---|---|---|---|---|---|---|---|---|---|
| 65 | | | | | 70 | | | | | 75 | | | | | 80 |

| Asp | Ser | Val | Lys | Gly | Arg | Phe | Thr | Ile | Ser | Arg | Asp | Thr | Ser | Lys | Asn |
|---|---|---|---|---|---|---|---|---|---|---|---|---|---|---|---|
| | | | | 85 | | | | | 90 | | | | | 95 | |

| Thr | Leu | Tyr | Leu | Gln | Met | Asn | Ser | Leu | Arg | Ala | Glu | Asp | Thr | Ala | Val |
|---|---|---|---|---|---|---|---|---|---|---|---|---|---|---|---|
| | | | 100 | | | | | 105 | | | | | 110 | | |

| Tyr | Tyr | Cys | Ala | Thr | Asp | Ser | Ser | Gly | Ser | Phe | Tyr | Glu | Tyr | Phe | Gln |
|---|---|---|---|---|---|---|---|---|---|---|---|---|---|---|---|
| | | | 115 | | | | | 120 | | | | | 125 | | |

| His | Trp | Gly | Gln | Gly | Thr | Leu | Val | Thr | Val | Ser | Ser |
|---|---|---|---|---|---|---|---|---|---|---|---|
| | 130 | | | | | 135 | | | | | 140 |

<210> SEQ ID NO 36
<211> LENGTH: 131
<212> TYPE: PRT
<213> ORGANISM: Homo Sapiens

<400> SEQUENCE: 36

| Met | Asp | Met | Arg | Val | Pro | Ala | Gln | Leu | Leu | Gly | Leu | Leu | Leu | Leu | Trp |
|---|---|---|---|---|---|---|---|---|---|---|---|---|---|---|---|
| 1 | | | | 5 | | | | | 10 | | | | | 15 | |

| Leu | Pro | Gly | Ala | Arg | Cys | Ala | Ile | Gln | Leu | Thr | Gln | Ser | Pro | Ser | Ser |
|---|---|---|---|---|---|---|---|---|---|---|---|---|---|---|---|
| | | | 20 | | | | | 25 | | | | | 30 | | |

| Leu | Ser | Ala | Ser | Val | Gly | Asp | Arg | Val | Thr | Ile | Thr | Cys | Arg | Ala | Ser |
|---|---|---|---|---|---|---|---|---|---|---|---|---|---|---|---|
| | | | 35 | | | | | 40 | | | | | 45 | | |

| Gln | Gly | Ile | Asn | Ser | Ala | Leu | Ala | Trp | Tyr | Gln | Gln | Lys | Pro | Gly | Lys |
|---|---|---|---|---|---|---|---|---|---|---|---|---|---|---|---|
| | 50 | | | | | 55 | | | | | 60 | | | | |

| Ala | Pro | Lys | Leu | Leu | Ile | Tyr | Asp | Ala | Ser | Ser | Leu | Glu | Ser | Gly | Val |
|---|---|---|---|---|---|---|---|---|---|---|---|---|---|---|---|
| 65 | | | | | 70 | | | | | 75 | | | | | 80 |

| Pro | Ser | Arg | Phe | Ser | Gly | Ser | Gly | Ser | Gly | Thr | Asp | Phe | Thr | Leu | Thr |
|---|---|---|---|---|---|---|---|---|---|---|---|---|---|---|---|
| | | | | 85 | | | | | 90 | | | | | 95 | |

| Ile | Ser | Ser | Leu | Gln | Pro | Glu | Asp | Phe | Ala | Thr | Tyr | Tyr | Cys | Gln | Gln |
|---|---|---|---|---|---|---|---|---|---|---|---|---|---|---|---|
| | | | 100 | | | | | 105 | | | | | 110 | | |

| Phe | Asn | Ser | Tyr | Pro | Tyr | Thr | Phe | Gly | Gln | Gly | Thr | Lys | Leu | Glu | Ile |
|---|---|---|---|---|---|---|---|---|---|---|---|---|---|---|---|
| | | | 115 | | | | | 120 | | | | | 125 | | |

| Lys | Arg | Thr |
|---|---|---|
| | 130 | |

<210> SEQ ID NO 37
<211> LENGTH: 363
<212> TYPE: DNA
<213> ORGANISM: Homo Sapiens

<400> SEQUENCE: 37

```
caggtgcagc tggtggagtc tgggggaggc gtggtccagc ctggggaggtc cctgagactc        60 tcctgtgcag cgtctggatt caccttcagt tgctgtggca tgcactgggt ccgccaggct       120
ccaggcaagg gctggagtg gtggcagtt atatggtatg atggaagtaa taaatactat       180
gcagactccg tgaagggccg attcaccatc tccagagaca cttccaagaa cacgctgtat       240
```

```
ctgcaaatga acagcctgag agccgaggac acggctgtgt attactgtgc gacagatagt      300
tcggggagtt tttatgaata cttccagcac tggggccagg gcaccctggt caccgtctcc      360
tca                                                                   363
```

<210> SEQ ID NO 38
<211> LENGTH: 327
<212> TYPE: DNA
<213> ORGANISM: Homo Sapiens

<400> SEQUENCE: 38

```
gccatccagt tgacccagtc tccatcctcc ctgtctgcat ctgtaggaga cagagtcacc       60
atcacttgcc gggcaagtca gggcattaac agtgctttag cctggtatca gcagaaacca      120
gggaaagctc ctaagctcct gatctatgat gcctccagtt tggaaagtgg ggtcccatca      180
aggttcagcg gcagtggatc tgggacagat ttcactctca ccatcagcag cctgcagcct      240
gaagattttg caacttatta ctgtcaacag tttaatagtt acccgtacac ttttggccag      300
gggaccaagc tggagatcaa acgaact                                          327
```

<210> SEQ ID NO 39
<211> LENGTH: 420
<212> TYPE: DNA
<213> ORGANISM: Homo Sapiens

<400> SEQUENCE: 39

```
atggagtttg ggctgagctg gttttcctc gttgctcttt taagaggtgt ccagtgtcag        60
gtgcagctgg tggagtctgg gggaggcgtg gtccagcctg gaggtccct gagactctcc       120 tgtgcagcgt ctggattcac cttcagttgc tgtggcatgc actgggtccg ccaggctcca      180
ggcaaggggc tggagtgggt ggcagttata tggtatgatg aagtaataa atactatgca       240 gactccgtga agggccgatt caccatctcc agagacactt ccaagaacac gctgtatctg      300
caaatgaaca gcctgagagc cgaggacacg gctgtgtatt actgtgcgac agatagttcg      360
ggagtttttt atgaatactt ccagcactgg ggccagggca cctggtcac cgtctcctca      420
```

<210> SEQ ID NO 40
<211> LENGTH: 393
<212> TYPE: DNA
<213> ORGANISM: Homo Sapiens

<400> SEQUENCE: 40

```
atggacatga gggtccccgc tcagctcctg gggcttctgc tgctctggct cccaggtgcc       60
agatgtgcca tccagttgac ccagtctcca tcctccctgt ctgcatctgt aggagacaga      120
gtcaccatca cttgccgggc aagtcagggc attaacagtg ctttagcctg gtatcagcag      180
aaaccaggga agctcctaa gctcctgatc tatgatgcct ccagtttgga aagtggggtc      240
ccatcaaggt tcagcggcag tggatctggg acagatttca ctctcaccat cagcagcctg      300
cagcctgaag attttgcaac ttattactgt caacagttta atagttaccc gtacactttt      360
ggccagggga ccaagctgga gatcaaacga act                                   393
```

<210> SEQ ID NO 41
<211> LENGTH: 121
<212> TYPE: PRT
<213> ORGANISM: Homo Sapiens

<400> SEQUENCE: 41

-continued

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Arg Gly Leu Asp Trp Val
        35                  40                  45

Ala Val Val Trp Tyr Asp Gly Tyr Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Gly Ser Phe Tyr Glu Tyr Leu Gln His Trp Gly
            100                 105                 110

Gln Gly Thr Leu Val Thr Val Ser Ser
            115                 120

<210> SEQ ID NO 42
<211> LENGTH: 110
<212> TYPE: PRT
<213> ORGANISM: Homo Sapiens

<400> SEQUENCE: 42

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro His
                85                  90                  95

Phe Trp Pro Gly Asp Gln Ala Gly Asp Gln Thr Asn Cys Gly
            100                 105                 110

<210> SEQ ID NO 43
<211> LENGTH: 140
<212> TYPE: PRT
<213> ORGANISM: Homo Sapiens

<400> SEQUENCE: 43

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Gly Tyr Gly Met His Trp Val Arg Gln Ala Pro Gly Arg Gly Leu
    50                  55                  60

Asp Trp Val Ala Val Val Trp Tyr Asp Gly Tyr Lys Phe Tyr Ala
65                  70                  75                  80

Asp Ser Val Lys Gly Arg Phe Thr Ile Ser Arg Asp Asn Ser Lys Asn
                85                  90                  95
```

Thr Leu Tyr Leu Gln Met Asn Ser Leu Arg Ala Glu Asp Thr Ala Val
            100                 105                 110

Tyr Tyr Cys Ala Arg Asp Ser Ser Gly Ser Phe Tyr Glu Tyr Leu Gln
            115                 120                 125

His Trp Gly Gln Gly Thr Leu Val Thr Val Ser Ser
            130                 135                 140

<210> SEQ ID NO 44
<211> LENGTH: 132
<212> TYPE: PRT
<213> ORGANISM: Homo Sapiens

<400> SEQUENCE: 44

Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Ala Leu Ala Trp Tyr Gln Gln Lys Pro Gly Lys
50                  55                  60

Ala Pro Lys Leu Leu Ile Tyr Asp Ala Ser Ser Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Tyr Pro His Phe Trp Pro Gly Asp Gln Ala Gly Asp Gln
            115                 120                 125

Thr Asn Cys Gly
            130

<210> SEQ ID NO 45
<211> LENGTH: 363
<212> TYPE: DNA
<213> ORGANISM: Homo Sapiens

<400> SEQUENCE: 45
caggtgcagt tggtggagtc tgggggaggc gtggtccagc ctggagggtc cctgagactc      60
tcctgtgcag cgtctggatt caccttcagt ggctatggca tgcactgggt ccgccaggct     120
ccaggcaggg ggctggactg ggtggcagtt gtgtggtatg atggaaggta taagttctat     180
gcagactccg tgaagggccg attcaccatc tccagagaca attccaagaa cacgctgtat     240
ctgcaaatga acagcctgag agccgaggac acggctgtgt attactgtgc gagagatagt     300
tcggggagtt tttatgaata cttacaacat tggggccagg gcaccctggt caccgtctcc     360
tca                                                                  363

<210> SEQ ID NO 46
<211> LENGTH: 325
<212> TYPE: DNA
<213> ORGANISM: Homo Sapiens

<400> SEQUENCE: 46
gccatccagt tgacccagtc tccatcctcc ctgtctgcat ctgtaggaga cagagtcacc      60
atcacttgcc gggcaagtca gggcattagc agtgctttag cctggtatca gcagaaacca     120
gggaaagctc ctaagctcct gatctatgat gcctccagtt tggaaagtgg ggtcccatca     180

```
aggttcagcg gcagtggatc tgggacagat tcactctca ccatcagcag cctgcagcct    240
gaagattttg caacttatta ctgtcaacag tttaatagtt accctcactt ttggccaggg    300
gaccaagctg gagatcaaac gaact                                          325

<210> SEQ ID NO 47
<211> LENGTH: 420
<212> TYPE: DNA
<213> ORGANISM: Homo Sapiens

<400> SEQUENCE: 47
atggagtttg ggctgagctg ggttttcctc gttgctcttt taagaggtgt ccagtgtcag     60
gtgcagttgg tggagtctgg gggaggcgtg gtccagcctg gaggtccct gagactctcc    120 tgtgcagcgt ctggattcac cttcagtggc tatggcatgc actgggtccg ccaggctcca    180 ggcaggggc tggactgggt ggcagttgtg tggtatgatg gaggttataa gttctatgca    240
gactccgtga agggccgatt caccatctcc agagacaatt ccaagaacac gctgtatctg    300
caaatgaaca gcctgagagc cgaggacacg gctgtgtatt actgtgcgag agatagttcg    360
gggagttttt atgaatactt acaacattgg ggccagggca ccctggtcac cgtctcctca    420

<210> SEQ ID NO 48
<211> LENGTH: 391
<212> TYPE: DNA
<213> ORGANISM: Homo Sapiens

<400> SEQUENCE: 48
atggacatga gggtccccgc tcagctcctg gggcttctgc tgctctggct cccaggtgcc     60
agatgtgcca tccagttgac ccagtctcca tcctccctgt ctgcatctgt aggagacaga    120
gtcaccatca cttgccgggc aagtcagggc attagcagtg ctttagcctg gtatcagcag    180
aaaccaggga aagctcctaa gctcctgatc tatgatgcct ccagtttgga aagtggggtc    240
ccatcaaggt tcagcggcag tggatctggg acagatttca ctctcaccat cagcagcctg    300
cagcctgaag attttgcaac ttattactgt caacagttta atagttaccc tcacttttgg    360
ccaggggacc aagctggaga tcaaacgaac t                                   391

<210> SEQ ID NO 49
<211> LENGTH: 10
<212> TYPE: PRT
<213> ORGANISM: Homo Sapiens

<400> SEQUENCE: 49

Gly Phe Thr Phe Ser Ser Tyr Ala Met His
1               5                   10

<210> SEQ ID NO 50
<211> LENGTH: 17
<212> TYPE: PRT
<213> ORGANISM: Homo Sapiens

<400> SEQUENCE: 50

Phe Ile Trp Asp Asp Gly Ser Phe Lys Tyr Tyr Ala Glu Ser Val Lys
1               5                   10                  15

Gly

<210> SEQ ID NO 51
<211> LENGTH: 9
<212> TYPE: PRT
```

<213> ORGANISM: Homo Sapiens

<400> SEQUENCE: 51

Glu Gly Ser Trp Ser Pro Asp Ile Phe
1               5

<210> SEQ ID NO 52
<211> LENGTH: 7
<212> TYPE: PRT
<213> ORGANISM: Homo Sapiens

<400> SEQUENCE: 52

Ser Gln Gly Ile Ser Arg Ala
1               5

<210> SEQ ID NO 53
<211> LENGTH: 3
<212> TYPE: PRT
<213> ORGANISM: Homo Sapiens

<400> SEQUENCE: 53

Asp Ala Ser
1

<210> SEQ ID NO 54
<211> LENGTH: 6
<212> TYPE: PRT
<213> ORGANISM: Homo Sapiens

<400> SEQUENCE: 54

Phe Asn Ser Tyr Pro Ile
1               5

<210> SEQ ID NO 55
<211> LENGTH: 10
<212> TYPE: PRT
<213> ORGANISM: Homo Sapiens

<400> SEQUENCE: 55

Gly Phe Thr Leu Ser Ser Phe Gly Met His
1               5                   10

<210> SEQ ID NO 56
<211> LENGTH: 17
<212> TYPE: PRT
<213> ORGANISM: Homo Sapiens

<400> SEQUENCE: 56

Val Ile Trp Tyr Asp Gly Ser Asn Glu Tyr Tyr Ala Asp Ser Val Lys
1               5                   10                  15
Gly

<210> SEQ ID NO 57
<211> LENGTH: 9
<212> TYPE: PRT
<213> ORGANISM: Homo Sapiens

<400> SEQUENCE: 57

Glu Gly Ser Trp Ser Pro Asp Ile Phe
1               5

<210> SEQ ID NO 58
<211> LENGTH: 7
<212> TYPE: PRT

<213> ORGANISM: Homo Sapiens

<400> SEQUENCE: 58

Ser Gln Gly Ile Arg Ser Ala
1               5

<210> SEQ ID NO 59
<211> LENGTH: 6
<212> TYPE: PRT
<213> ORGANISM: Homo Sapiens

<400> SEQUENCE: 59

Phe Asn Ser Tyr Pro Val
1               5

<210> SEQ ID NO 60
<211> LENGTH: 10
<212> TYPE: PRT
<213> ORGANISM: Homo Sapiens

<400> SEQUENCE: 60

Gly Phe Thr Leu Ser Ser Tyr Gly Met His
1               5                   10

<210> SEQ ID NO 61
<211> LENGTH: 17
<212> TYPE: PRT
<213> ORGANISM: Homo Sapiens

<400> SEQUENCE: 61

Val Ile Trp Tyr Asp Gly Asn Asn Gln Tyr Tyr Ala Asp Ser Val Lys
1               5                   10                  15

Gly

<210> SEQ ID NO 62
<211> LENGTH: 9
<212> TYPE: PRT
<213> ORGANISM: Homo Sapiens

<400> SEQUENCE: 62

Glu Gly Ser Trp Ser Pro Asp Ile Phe
1               5

<210> SEQ ID NO 63
<211> LENGTH: 7
<212> TYPE: PRT
<213> ORGANISM: Homo Sapiens

<400> SEQUENCE: 63

Ser Gln Gly Ile Ser Ser Tyr
1               5

<210> SEQ ID NO 64
<211> LENGTH: 5
<212> TYPE: PRT
<213> ORGANISM: Homo Sapiens

<400> SEQUENCE: 64

Phe Asn Ser Tyr Pro
1               5

<210> SEQ ID NO 65
<211> LENGTH: 10
<212> TYPE: PRT

<213> ORGANISM: Homo Sapiens

<400> SEQUENCE: 65

Gly Asp Thr Phe Ser Ser Tyr Ala Ile Ser
1               5                   10

<210> SEQ ID NO 66
<211> LENGTH: 17
<212> TYPE: PRT
<213> ORGANISM: Homo Sapiens

<400> SEQUENCE: 66

Gly Ile Ile Pro Val Ile Gly Thr Val Asn Tyr Glu Glu Arg Phe Gln
1               5                   10                  15
Asp

<210> SEQ ID NO 67
<211> LENGTH: 5
<212> TYPE: PRT
<213> ORGANISM: Homo Sapiens

<400> SEQUENCE: 67

Glu Glu Gly Phe Leu
1               5

<210> SEQ ID NO 68
<211> LENGTH: 7
<212> TYPE: PRT
<213> ORGANISM: Homo Sapiens

<400> SEQUENCE: 68

Ser Gln Gly Ile Ser Ser Ala
1               5

<210> SEQ ID NO 69
<211> LENGTH: 6
<212> TYPE: PRT
<213> ORGANISM: Homo Sapiens

<400> SEQUENCE: 69

Phe Asn Ser Tyr Pro Leu
1               5

<210> SEQ ID NO 70
<211> LENGTH: 10
<212> TYPE: PRT
<213> ORGANISM: Homo Sapiens

<400> SEQUENCE: 70

Gly Phe Thr Phe Ser Cys Cys Gly Met His
1               5                   10

<210> SEQ ID NO 71
<211> LENGTH: 17
<212> TYPE: PRT
<213> ORGANISM: Homo Sapiens

<400> SEQUENCE: 71

Val Ile Trp Tyr Asp Gly Ser Asn Lys Tyr Tyr Ala Asp Ser Val Lys
1               5                   10                  15
Gly

<210> SEQ ID NO 72

```
<211> LENGTH: 10
<212> TYPE: PRT
<213> ORGANISM: Homo Sapiens

<400> SEQUENCE: 72

Asp Ser Ser Gly Ser Phe Tyr Glu Tyr Phe
1               5                   10

<210> SEQ ID NO 73
<211> LENGTH: 7
<212> TYPE: PRT
<213> ORGANISM: Homo Sapiens

<400> SEQUENCE: 73

Ser Gln Gly Ile Asn Ser Ala
1               5

<210> SEQ ID NO 74
<211> LENGTH: 6
<212> TYPE: PRT
<213> ORGANISM: Homo Sapiens

<400> SEQUENCE: 74

Phe Asn Ser Tyr Pro Tyr
1               5

<210> SEQ ID NO 75
<211> LENGTH: 10
<212> TYPE: PRT
<213> ORGANISM: Homo Sapiens

<400> SEQUENCE: 75

Gly Phe Thr Phe Ser Gly Tyr Gly Met His
1               5                   10

<210> SEQ ID NO 76
<211> LENGTH: 17
<212> TYPE: PRT
<213> ORGANISM: Homo Sapiens

<400> SEQUENCE: 76

Val Val Trp Tyr Asp Gly Gly Tyr Lys Phe Tyr Ala Asp Ser Val Lys
1               5                   10                  15

Gly

<210> SEQ ID NO 77
<211> LENGTH: 10
<212> TYPE: PRT
<213> ORGANISM: Homo Sapiens

<400> SEQUENCE: 77

Asp Ser Ser Gly Ser Phe Tyr Glu Tyr Leu
1               5                   10

<210> SEQ ID NO 78
<211> LENGTH: 7
<212> TYPE: PRT
<213> ORGANISM: Homo Sapiens

<400> SEQUENCE: 78

Ser Gln Gly Ile Ser Ser Ala
1               5

<210> SEQ ID NO 79
```

-continued

```
<211> LENGTH: 6
<212> TYPE: PRT
<213> ORGANISM: Homo Sapiens

<400> SEQUENCE: 79

Phe Asn Ser Tyr Pro His
1               5
```

HUMAN MONOCLONAL ANTIBODIES AGAINST HUMAN IL-4

This application is the National Stage of International Application No. PCT/EP2005/008361 filed on Aug 2, 2005, which claims benefit under 35 U.S.C. §119(e) of Great Britain application numbers 0147301.9, 0147302.7, 0147303.5, 0147304.3, 0147305.0, and 0147306.8, all of which were filed Aug. 3, 2004.

The present invention relates to antibodies which are specific for human interleukin-4 (hIL-4).

Allergic diseases such as atopic dermatitis, allergic rhinitis, asthma and food allergies are characteristically associated with exacerbated Th2 cell responses to innocuous environmental antigens (allergens). Allergens are captured by antigen presenting cells, processed and presented in the context of MHC Class II molecules to allergen-specific T helper (Th) cells. Allergen specific Th cells belong to the Th2 phenotype and develop from precursor T cells under the influence of interleukin-4 (IL-4). Once Th2 cells are activated, they secrete IL-4 and interleukin-13 (IL-13), which together with surface bound signals induce B cells to switch to IgE producing plasma cells. IgE molecules bind to high affinity FcεR on mast cells and, after subsequent encounter with allergen, induce mast cell activation and the release of mediators of allergic reactions. Th2 cytokines also promote the survival of eosinophils and the growth of mast cells which, after degranulation, also release additional Th2 cytokines capable of augmenting IgE production, Th2 cell differentiation and eosinophil survival. Thus, Th2 cells play a pivotal role in the induction and development of allergic responses and therefore, antagonizing their development and/or their effector functions would be an efficient way to intervene in allergic responses.

IL-4 and IL-13 share many biological activities due to the fact that both cytokines use the IL-4 receptor (IL-4R)-alpha chain as a component of their respective receptor complexes. IL-13 signals through an heterodimeric complex consisting of an IL-13 binding chain (IL-13Rα1) and the IL-4Rα chain. IL-4 utilizes this IL-4Rα/IL-13Rα1 complex, called type II IL-4R, as an alternative to the type IL-4R, consisting of IL-4Rα chain and the common γ chain (cγ) shared by receptors for IL-2, IL-4, IL-7, IL-9, IL-15 and thymic stromal lymphopoietin (TSLP). Because T cells do not express IL-13Rα1, IL-13 in contrast to IL-4 does not support T cell proliferation and cannot induce the differentiation of naïve human Th cells towards the Th2 phenotype (see e.g. J. E. de Vries et al., Encyclopedia of Hormones and related cell regulators, Academic Press, 2002). IL-4 plays a pivotal role in T cell proliferation and thus in the development and maintenance of allergic diseases. IL-4 gene deficient mice or mice lacking IL-4 (see e.g. Kuhn R. et al., Science, 1991 (5032) 707:10) or the downstream signaling factor STAT6 (see e.g. Kaplan M. H. et al., Immunity, 1996 (3) 313-9) do not develop significant numbers of Th2 cells and have reduced IgE responses.

We have now found antibodies with a high affinity for human IL-4 and a strong inhibitory potential of IL-4 mediated IgE synthesis by naïve human B cells.

In one aspect the present invention provides an human IL-4 specific antibody which binds to human IL-4 with a dissociation constant $K_d$ of equal or less than 800 pM, such as e.g. equal or less than 200 pM.

In another aspect the present invention provides an antibody having a first domain comprising in sequence the hypervariable regions CDR1, CDR2 and CDR3 and a second domain comprising in secquence the hypervariable regions CDR1', CDR2' and CDR3' selected from the group consisting of an antibody wherein a) said CDR1 has the amino acid sequence Gly-Phe-Thr-Phe-Ser-Ser-Tyr-Ala-Met-His (GFTFSSYAMH) (SEQ ID NO: 49),
said CDR2 has the amino acid sequence Phe-Ile-Trp-Asp-Asp-Gly-Ser-Phe-Lys-Tyr-Tyr-Ala-Glu-Ser-Val-Lys-Gly (FIWDDGSFKYYAESVKG) (SEQ ID NO: 50),
said CDR3 has the amino acid sequence Glu-Gly-Ser-Trp-Ser-Pro-Asp-Ile-Phe (EGSWSPDIF) (SEQ ID NO: 51),
said CDR1' has the amino acid sequence Ser-Gln-Gly-Ile-Ser-Arg-Ala (SQGISRA) (SEQ ID NO: 52),
said CDR2' has the amino acid sequence Asp-Ala-Ser (DAS) (SEQ ID NO: 53),
said CDR3' has the amino acid sequence Phe-Asn-Ser-Tyr-Pro-Ile (FNSYPI) (SEQ ID NO: 54), b) said CDR1 has the amino acid sequence Gly-Phe-Thr-Leu-Ser-Ser-Phe-Gly-Met-His (GFTLSSFGMH) (SEQ ID NO: 55),
said CDR2 has the amino acid sequence Val-Ile-Trp-Tyr-Asp-Gly-Ser-Asn-Glu-Tyr-Tyr-Ala-Asp-Ser-Val-Lys-Gly (VIWYDGSNEYYADSVKG) (SEQ ID NO: 56),
said CDR3 has the amino acid sequence Glu-Gly-Ser-Trp-Ser-Pro-Asp-Ile-Phe (EGSWSPDIF) (SEQ ID NO: 57),
said CDR1' has the amino acid sequence Ser-Gln-Gly-Ile-Arg-Ser-Ala (SQGIRSA) (SEQ ID NO: 58),
said CDR2' has the amino acid sequence Asp-Ala-Ser (DAS) (SEQ ID NO: 53),
said CDR3' has the amino acid sequence Phe-Asn-Ser-Tyr-Pro-Val (FNSYPV) (SEQ ID NO: 59), c) said CDR1 has the amino acid sequence Gly-Phe-Thr-Leu-Ser-Ser-Tyr-Gly-Met-His (GFTLSSYGMH) (SEQ ID NO: 60),
said CDR2 has the amino acid sequence Val-Ile-Trp-Asp-Gly-Asn-Asn-Gln-Tyr-Tyr-Ala-Asp-Ser-Val-Lys-Gly (VIWYDGNNQYYADSVKG) (SEQ ID NO: 61),
said CDR3 has the amino acid sequence Glu-Gly-Ser-Trp-Ser-Pro-Asp-Ile-Phe (EGSWSPDIF) (SEQ ID NO: 62),
said CDR1' has the amino acid sequence Ser-Gin-Gly-Ile-Ser-Ser-Tyr (SQGISSY) (SEQ ID NO: 63),
said CDR2' has the amino acid sequence Asp-Ala-Ser (DAS) (SEQ ID NO: 53),
said CDR3' has the amino acid sequence Phe-Asn-Ser-Tyr-Pro (FNSYP) (SEQ ID NO: 64), d) said CDR1' has the amino acid sequence Gly-Asp-Thr-Phe-Ser-Ser-Tyr-Ala-Ile-Ser (GDTFSSYAIS) (SEQ ID NO: 65),
said CDR2 has the amino acid sequence Gly-Ile-Ile-Pro-Val-Ile-Gly-Thr-Val-Asn-Tyr-Glu-Glu-Arg-Phe-Gln-Asp (GIIPVIGTVNYEERFQD) (SEQ ID NO: 66),
said CDR3 has the amino acid sequence Glu-Glu-Gly-Phe-Leu (EEGFL) (SEQ ID NO: 67),
said CDR1' has the amino acid sequence Ser-Gin-Gly-Ile-Ser-Ser-Ala (SQGISSA) (SEQ ID NO: 68),
said CDR2 has the amino acid sequence Asp-Ala-Ser (DAS) (SEQ ID NO: 53),
said CDR3' has the amino acid sequence Phe-Asn-Ser-Tyr-Pro-Leu (FNSYPL) (SEQ ID NO: 69), e) said CDR 1 has ' the amino acid sequence Gly-Phe-Thr-Phe-Ser-Cys-Cys-Gly-Met-His (GFTFSCCGMH) (SEQ ID NO: 70),
said CDR2 has the amino acid sequence Val-Ile-Trp-Tyr-Asp-Gly-Ser-Asn-Lys-Tyr-Tyr-Ala-Asp-Ser-Val-Lys-Gly (VIWYDGSNKYYADSVKG) (SEQ ID NO: 71), said CDR3 has the amino acid sequence Asp-Ser-Ser-Gly-Ser-Phe-Tyr-Glu-Tyr-Phe (DSSGSFYEYF) (SEQ ID NO: 72),
said CDR1' has the amino acid sequence Ser-Gln-Gly-Ile-Asn-Ser-Ala (SQGINSA) (SEQ ID NO: 73),
said CDR2' has the amino acid sequence Asp-Ala-Ser (DAS) (SEQ ID NO: 53),
said CDR3' has the amino acid sequence Phe-Asn-Ser-Tyr-Pro-Tyr (FNSYPY) (SEQ ID NO: 74), and
f) said CDR1' has the amino acid sequence Gly-Phe-Thr-Phe-Ser-Gly-Tyr-Gly-Met-His (GFTFSGYGMH) (SEQ ID NO: 75),
said CDR2 has the amino acid sequence Val-Val-Trp-Tyr-Asp-Gly-Gly-Tyr-Lys-Phe-Tyr-Ala-Asp-Ser-Val-Lys-Gly (VVWYDGGYKFYADSVKG) (SEQ ID NO: 76),
said CDR3 has the amino acid sequence Asp-Ser-Ser-Gly-Ser-Phe-Tyr-Glu-Tyr-Leu (DSSGSFYEYL) (SEQ ID NO: 77),
said CDR1' has the amino acid sequence Ser-Gin-Gly-Ile-Ser-Ser-Ala (SQGISSA) (SEQ ID NO: 78),
said CDR2' has the amino acid sequence Asp-Ala-Ser (DAS) (SEQ ID NO: 53),
said CDR3' has the amino acid sequence Phe-Asn-Ser-Tyr-Pro-His (FNSYPH) (SEQ ID NO: 79).

CDR1, CDR2 and CDR3 are part of the amino acid sequence of the heavy chain of such antibody and CDR1', CDR2' and CDR3' are part of the amino acid sequence of the light chain of such antibody.

We also have found an antibody comprising:
the amino acid sequence of the heavy chain of a mature polypeptide of SEQ ID NO:1 and the amino acid sequence of the light chain of a mature polypeptide of SEQ ID NO:2, or
the amino acid sequence of the heavy chain of a mature polypeptide of SEQ ID NO:9 and the amino acid sequence of the light chain of a mature polypeptide of SEQ ID NO:10, or
the amino acid sequence of the heavy chain of a mature polypeptide of SEQ ID NO:17 and the amino acid sequence of the light chain of a mature polypeptide of SEQ ID NO:18, or
the amino acid sequence of the heavy chain of a mature polypeptide of SEQ ID NO:25 and the amino acid sequence of the light chain of a mature polypeptide of SEQ ID NO:26, or
the amino acid sequence of the heavy chain of a mature polypeptide of SEQ ID NO:33 and the amino acid sequence of the light chain of a mature polypeptide of SEQ ID NO:34, or
the amino acid sequence of the heavy chain of a mature polypeptide of SEQ ID NO:41 and the amino acid sequence of the light chain of a mature polypeptide of SEQ ID NO:42.

In a further aspect the present invention provides an antibody comprising
a) a polypeptide of SEQ ID NO:1 and a polypeptide of SEQ ID NO:2, or
b) a polypeptide of SEQ ID NO:9 and a polypeptide of SEQ ID NO:10, or
c) a polypeptide of SEQ ID NO:17 and a polypeptide of SEQ ID NO:18, or
d) a polypeptide of SEQ ID NO:25 and a polypeptide of SEQ ID NO:26, or
e) a polypeptide of SEQ ID NO:33 and a polypeptide of SEQ ID NO:34, or
f) a polypeptide of SEQ ID NO:41 and a polypeptide of SEQ ID NO:42.

We further have found an antibody comprising:
the amino acid sequence of the heavy chain of a polypeptide of SEQ ID NO:1 further containing a leader sequence (=SEQ ID NO:3) and the amino acid sequence of the light chain of a polypeptide of SEQ ID NO:2 further containing a leader sequence (=SEQ ID NO:4), or
the amino acid sequence of the heavy chain of a polypeptide of SEQ ID NO:9 further containing a leader sequence (=SEQ ID NO:11) and the amino acid sequence of the light chain of a polypeptide of SEQ ID NO:10 further containing a leader sequence (=SEQ ID NO:12), or
the amino acid sequence of the heavy chain of a polypeptide of SEQ ID NO:17 further containing a leader sequence (=SEQ ID NO:19) and the amino acid sequence of the light chain of a polypeptide of SEQ ID NO:18 further containing a leader sequence (=SEQ ID NO:20), or
the amino acid sequence of the heavy chain of a polypeptide of SEQ ID NO:25 further containing a leader sequence (=SEQ ID NO:27) and the amino acid sequence of the light chain of a polypeptide of SEQ ID NO:26 further containing a leader sequence (=SEQ ID NO:28), or
the amino acid sequence of the heavy chain of a polypeptide of SEQ ID NO:33 further containing a leader sequence (=SEQ ID NO:35) and the amino acid sequence of the light chain of a polypeptide of SEQ ID NO:34 further containing a leader sequence (=SEQ ID NO:36), or
the amino acid sequence of the heavy chain of a polypeptide of SEQ ID NO:41 further containing a leader sequence (=SEQ ID NO:43) and the amino acid sequence of the light chain of a polypeptide of SEQ ID NO:42 further containing a leader sequence (=SEQ ID NO:44).

In a further aspect the present invention provides an antibody comprising
a) a polypeptide of SEQ ID NO:3 and a polypeptide of SEQ ID NO:4, or
b) a polypeptide of SEQ ID NO:11 and a polypeptide of SEQ ID NO:12, or
c) a polypeptide of SEQ ID NO:19 and a polypeptide of SEQ ID NO:20, or
d) a polypeptide of SEQ ID NO:27 and a polypeptide of SEQ ID NO:28, or
e) a polypeptide of SEQ ID NO:35 and a polypeptide of SEQ ID NO:36, or
f) a polypeptide of SEQ ID NO:43 and a polypeptide of SEQ ID NO:44.

Antibodies provided by the present invention are hereinafter also designated as "compound(s) of (according to) the present invention".

In another aspect the present invention provides a compound of the present invention which is selected from the group consisting of an human IL-4 specific monoclonal antibody (hIL-4 mAb), a fragment thereof and an analog thereof.

An hIL-4 mAb is an antibody which specifically recognizes human IL-4, i.e. includes antigen binding sites specific for human IL-4, and which has specifically its CDRs but also other parts of the heavy and light chain derived from human immunoglobulins.

The antibody may be of any isotype including IgG1, IgG2, IgG3 and IgG4, preferably of isotype IgG1.

"A fragment thereof" means a part of the heavy and light chain variable sequence of a hIL-4 mAb, which retains the same antigen binding specificity and/or neutralizing ability as the molecule from which the fragments are derived, e.g. a Fab fragment or a F(ab')$_2$ fragment derived from hIL-4 mAb.

A Fab fragment contains the entire light chain and amino terminal portions of the heavy chain; a F(ab')$_2$ fragment is the fragment formed by 2 Fab fragments bound by disulfide bonds. Such fragments can be obtained by conventional means, e.g. cleavage of the monoclonal antibodies with the appropriate proteolytic enzymes, papain and/or pepsin, or by recombinant methods, and the fragments themselves are useful as therapeutic and/or prophylactic agents.

"An analog thereof" means a hIL-4 mAb with an amino acid sequence which is modified by at least one amino acid outside of the CDR regions, e.g. outside of CDR1, CDR2 and CDR3 of the heavy chain or outside of CDR1', CDR2' and CDR3' of the light chain. Said modification includes a chemical modification, a substitution or a rearrangement of one or a few amino acids, i.e. no more than 10 amino acids, which modification permits the amino acid sequence to retain the biological characteristics, e.g. antigen specificity and affinity, of the unmodified sequence. For example silent mutations can be constructed via substitution to create endonuclease restriction sites within or surrounding the CDR regions.

An analog may also arise as allelic variation. An "allelic variation or modification" is an alteration in the nucleic acid sequence encoding an antibody of the present invention outside of the CDR regions. Such alterations or modifications may be due to the degeneracies of the genetic code or may be liberately engineered to provide desired characteristics. Such variations or modifications may or may not result in alterations in any encoded amino acid sequence, but retain the biological activities, e.g. antigen specificity and affinity.

We have also found polynucleotides encoding compounds of the present invention.

In another aspect the present invention provides isolated polynucleotides comprising polynucleotides encoding a compound of the present invention.

In another aspect the present invention provides polynucleotides encoding the amino acid sequence of CDR1, CDR2 and CDR3 of a compound of the present invention and polynucleotides encoding the amino acid sequence of CDR1', CDR2' and CDR3' of a compound of the present invention.

In another aspect the present invention provides polynucleotides comprising a) a polynucleotide of SEQ ID NO:5 and a polynucleotide of SEQ ID NO:6, or
b) a polynucleotide of SEQ ID NO:13 and a polynucleotide of SEQ ID NO:14, or
c) a polynucleotide of SEQ ID NO:21 and a polynucleotide of SEQ ID NO:22, or
d) a polynucleotide of SEQ ID NO:29 and a polynucleotide of SEQ ID NO:30, or
e) a polynucleotide of SEQ ID NO:37 and a polynucleotide of SEQ ID NO:38, or
f) a polynucleotide of SEQ ID NO:45 and a polynucleotide of SEQ ID NO:46.

In another aspect the present invention provides polynucleotides encoding a) a polypeptide of SEQ ID NO:7 and SEQ ID NO:8, or
b) a polypeptide of SEQ ID NO:15 and SEQ ID NO:16, or
c) a polypeptide of SEQ ID NO:23 and SEQ ID NO:24, or
d) a polypeptide of SEQ ID NO:31 and SEQ ID NO:32, or
e) a polypeptide of SEQ ID NO:39 and SEQ ID NO:40, or
f) a polypeptide of SEQ ID NO:47 and SEQ ID NO:48.

SEQ ID NO:5 is a polynucleotide encoding an amino acid sequence of SEQ ID NO:1.
SEQ ID NO:6 is a polynucleotide encoding an amino acid sequence of SEQ ID NO:2.
SEQ ID NO:7 is a polynucleotide encoding an amino acid sequence of SEQ ID NO:3.
SEQ ID NO:8 is a polynucleotide encoding an amino acid sequence of SEQ ID NO:4.
SEQ ID NO:13 is a polynucleotide encoding an amino acid sequence of SEQ ID NO:9.
SEQ ID NO:14 is a polynucleotide encoding an amino acid sequence of SEQ ID NO:10.
SEQ ID NO:15 is a polynucleotide encoding an amino acid sequence of SEQ ID NO:11.
SEQ ID NO:16 is a polynucleotide encoding an amino acid sequence of SEQ ID NO:12.
SEQ ID NO:21 is a polynucleotide encoding an amino acid sequence of SEQ ID NO:17.
SEQ ID NO:22 is a polynucleotide encoding an amino acid sequence of SEQ ID NO:18.
SEQ ID NO:23 is a polynucleotide encoding an amino acid sequence of SEQ ID NO:19.
SEQ ID NO:24 is a polynucleotide encoding an amino acid sequence of SEQ ID NO:20.
SEQ ID NO:29 is a polynucleotide encoding an amino acid sequence of SEQ ID NO:25.
SEQ ID NO:30 is a polynucleotide encoding an amino acid sequence of SEQ ID NO:26.
SEQ ID NO:31 is a polynucleotide encoding an amino acid sequence of SEQ ID NO:27.
SEQ ID NO:32 is a polynucleotide encoding an amino acid sequence of SEQ ID NO:28.
SEQ ID NO:37 is a polynucleotide encoding an amino acid sequence of SEQ ID NO:33.
SEQ ID NO:38 is a polynucleotide encoding an amino acid sequence of SEQ ID NO:34.
SEQ ID NO:39 is a polynucleotide encoding an amino acid sequence of SEQ ID NO:35.
SEQ ID NO:40 is a polynucleotide encoding an amino acid sequence of SEQ ID NO:36.
SEQ ID NO:45 is a polynucleotide encoding an amino acid sequence of SEQ ID NO:41.
SEQ ID NO:46 is a polynucleotide encoding an amino acid sequence of SEQ ID NO:42.
SEQ ID NO:47 is a polynucleotide encoding an amino acid sequence of SEQ ID NO:43.
SEQ ID NO:48 is a polynucleotide encoding an amino acid sequence of SEQ ID NO:44.

A compound of the present invention may be produced by recombinant DNA techniques. Thus, one or more DNA molecules encoding the antibody, a fragment thereof or an analog thereof may be constructed, placed under appropriate control sequences in an appropriate vector and transferred into a suitable host (organism) for expression. The compound of the present invention may be obtained according, e.g. analogously, to a method as conventional together with the information provided herein, e.g. with the knowledge of the amino acid sequence of the hypervariable and/or variable regions and the polynucleotides encoding these regions. A method for constructing a variable domain gene is e.g. described in EP 239 400 and may be briefly summarized as follows:

A replicable expression vector including a suitable promoter operably linked to a polynucleotide sequence of interest, e.g. encoding at least a variable domain of an immunoglobulin heavy or light chain comprising CDRs, is prepared, a suitable cell line is transformed with said expression vector, the transformed cell line is cultured and the corresponding immunoglobulin is obtained.

In another aspect the present invention provides an expression vector comprising a polynucleotide encoding a compound of the present invention, e.g. at least one polynucleotide of SEQ ID NO:5, SEQ ID NO: 6, SEQ ID NO:7, SEQ ID No:8, SEQ ID NO:13, SEQ ID NO:14, SEQ ID NO:15, SEQ ID No:16, SEQ ID NO:21, SEQ ID NO:22, SEQ ID NO:23, SEQ ID No:24, SEQ ID NO:37, SEQ ID NO:38, SEQ ID NO:39, SEQ ID No:40, SEQ ID NO:45, SEQ ID NO:46, SEQ ID NO:47 or SEQ ID No:48.

Naturally an expression vector can comprise more than one polynucleotide.

In another aspect the present invention provides

An expression system comprising a polynucleotide encoding a compound of the present invention wherein said expression system or part thereof is capable of producing a compound of the present invention, e.g. a hIL-4 mAb, when said expression system or part thereof is present in a compatible host cell; and An isolated host cell comprising an expression system as defined above.

Expression vectors, e.g. comprising suitable promoter(s) and genes encoding heavy and light chain constant parts are known, e.g. and are commercially available and include e.g. heavy chain vector IgG1 and light chain vector human kappa. A conventional expression vector or recombinant plasmid may be produced by placing the respective polynucleotide in operative association with conventional regulatory control sequences capable of controlling the replication and expression in, and/or secretion from, a host cell. Regulatory sequences include promoter sequences, e.g. CMV promoter, LCK promoter, and appropriate signal sequences.

A selected host cell may be transfected by conventional techniques with the vector of interest to create a transfected host cell, which then may be cultured by conventional techniques to produce the compounds of the present invention.

Appropriate cell lines may be found according, e.g. analogously, to a method as conventional. Appropriate hosts are known or may be found according, e.g. analogously, to a method as conventional and include cell cultures or transgenic animals.

Suitable host cells or cell lines for the expression of the compounds of the present invention are preferably eukaryotic cells such as e.g. CHO, COS, a fibroblast cell (e.g. 3T3) and myeloid cells among others, preferably a mammalian cell, such as a CHO cell or SP2/0.

The compounds of the present invention exhibit pharmacological activity and are therefore useful as pharmaceuticals. E.g., the compounds of the present invention interfere strongly with the binding of IL-4 to an IL4 receptor and are herein also referred to as IL-4 blocking or neutralizing compounds of the present invention, including hIL-4 mAb(s). Compounds of the present invention show activity and their affinity can be determined in the TEST:AFFINITY MEASUREMENT as described in Example 1.

A compound of the present invention thus shows therapeutic activity against IL4 and/or IgE mediated diseases, such as various allergic diseases, e.g. including urticaria, allergic reactions to medication, rhinitis, e.g. allergic rhinitis, conjunctivitis, e.g. rhinoconjunctivitis, dermatitis, e.g. atopic dermatitis, asthma, e.g. atopic asthma and allergic asthma, anaphylactic shock; preferably atopic dermatitis, allergic asthma, allergic rhinitis, allergic rhinoconjunctivitis, such as allergic asthma or atopic dermatitis;

autoimmune diseases, including e.g. Kawasaki disease, Grave's disease, Sjorgen's syndrome, autoimmune lymphoproliferative syndrome, autoimmune haemolytic anemia, autoimmune uveitis, myasthenia gravis, Lupus Erythematosis and Bullous pemphigoid;

disorders of the digestive system. in which IL-4 and/or IgE play a role, including e.g. ulcers, gastric inflammation, mucosal inflammation, ulcerative colitis, Crohn's disease, inflammatory bowel disease and other disorders of the digestive system in which IL4 and/or IgE play a role;

diseases wherein IL-4 and/or IgE are overproduced and considered to contribute to pathology, including e.g. systemic sclerosis (scleroderma), septic arthritis and reactive arthritis.

In another aspect the present invention provides a compound of the present invention, e.g. a hIL-4 mAb, for use as a pharmaceutical, e.g. against IL4 and/or IgE mediated diseases, e.g. allergic diseases, e.g. atopic dermatitis, allergic asthma, allergic rhinitis, preferably atopic dermatitis.

In another aspect the present invention provides the use of the present invention of a compound of the present invention which is selected from the group consisting of a hIL-4 mAb, a fragment thereof and an analog thereof.

For pharmaceutical use a compound of the present invention includes one or more, preferably one, compounds of the present invention, e.g. a combination of two or more compounds of the present invention.

In another aspect the present invention provides the use of a compound of the present invention for the manufacture of a medicament, e.g. a pharmaceutical composition, for the treatment of diseases mediated by IL4 and/or IgE, e.g. allergic diseases, e.g. allergic rhinoconjunctivitis, atopic dermatitis, allergic asthma, allergic rhinitis, preferably allergic asthma or atopic dermatitis, such as atopic dermatitis.

In a further aspect the present invention provides the use of a compound of the present invention for the manufacture of a medicament, e.g. a pharmaceutical composition, for the treatment of a disease as described above, e.g. selected from the group consisting of atopic dermatitis, allergic asthma and allergic rhinitis.

In a further aspect the present invention provides a compound of the present invention for the uses as mentioned above, wherein the compound of the present invention is selected from the group consisting of a hIL-4 mAb, a fragment thereof and an analog thereof.

It has, for example been determined that the affinity constant of a compound of the present invention, e.g. a hIL-4 mAb, a fragment thereof or an analog thereof, for human IL-4 is equal or less than 800 pM, e.g. is equal or less than 200 pM, such as of about 30 pM to about 200 pM, preferably of about 45 pM to about 170 pM, such as about 100 pM, more preferred about 50 pM, such as about 45 pM.

It has, for example also been determined that the affinity constant of a compound of the present invention, e.g. a hIL-4 mAb, a fragment thereof or an analog thereof, for human IL4 is of 30 pM to 200 pM, preferably of 45 pM to 170 pM, such as 100 pM, more preferred 50 pM, such as 45 pM.

It is therefore, indicated that for the treatment of diseases mediated by IL4, the compounds of the present invention may be administered to larger mammals, for example humans, by similar modes of administration at similar dosages than conventionally used with monoclonal antibodies.

In another aspect the present invention provides an antibody which binds to human IL4 with a dissociation constant of equal or less than 200 pM, e.g. 30 to 200 pM.

In a further aspect of the present invention the antibody for the uses as mentioned above is a hIL-4 mAb, a fragment thereof or an analog thereof which binds to human IL4 with a dissociation constant $K_d$ of equal or less than 200 pM, e.g. 30 to 200 pM.

In a further aspect the present invention provides a method of treatment of diseases which are mediated by IL-4 and/or IgE, e.g. allergic diseases, e.g. atopic dermatitis, allergic asthma, allergic rhinitis, preferably atopic dermatitis, which treatment comprises administering to a subject in need of such treatment an effective amount of a compound of the present invention; e.g. in the form of a pharmaceutical composition.

In a further aspect of the present invention a compound of the present invention is administered in combination with another pharmaceutically active agent either simultaneously or in sequence. Treatment includes treatment and prophylaxis.

For such treatment, the appropriate dosage will, of course, vary depending upon, for example, the chemical nature and the pharmacokinetic data of an antibody of the present invention employed, the individual host, the mode of administration and the nature and severity of the conditions being treated. However, in general, for satisfactory results in larger mammals, for example humans, an indicated daily dosage is in the range from, e.g. about, 0.1 ng/kg to, e.g. about, 10 mg/kg, such as from, e.g. about, 100 ng/kg to, e.g. about, 2 mg/kg of a compound of the present invention; conveniently administered, for example, in divided doses up to four times a day.

A compound of the present invention may be administered by any conventional route, for example parenterally, e.g. including intravenous, intradermal, intramuscular, subcutaneous, intranasal administration, injectable solutions or suspensions or inhaler powder.

In another aspect the present invention provides a pharmaceutical composition comprising a compound of the present invention in association with at least one pharmaceutical excipient, e.g. appropriate carrier and/or diluent, e.g. including fillers, binders, disintegrators, flow conditioners, lubricants, sugars and sweeteners, fragrances, preservatives, stabilizers, wetting agents and/or emulsifiers, solubilizers, salts for regulating osmotic pressure and/or buffers.

In another aspect the present invention provides a pharmaceutical composition according to the present invention further comprising another pharmaceutically active agent.

Such compositions may be manufactured according, e.g. analogously to a method as conventional, e.g. by mixing, granulating, coating, dissolving or lyophilizing processes. Unit dosage forms may contain, for example, from, e.g. about, 0.5 mg to, e.g. about, 1000 mg, such as 1 mg to about 500 mg.

A compound of the present invention may be used for pharmaceutical treatment according to the present invention alone or in combination with one or more other pharmaceutically active agents. Such other pharmaceutically active agents include e.g. other antibodies, e.g. such as antibodies neutralizing IgE, cytokines or cytokine receptors, which are chosen according to the particular condition to be treated.

Combinations include fixed combinations, in which two or more pharmaceutically active agents are in the same formulation; kits, in which two or more pharmaceutically active agents in separate formulations are sold in the same package, e.g. with instruction for co-administration; and free combinations in which the pharmaceutically active agents are packaged separately, but instruction for simultaneous or sequential administration are given.

In another aspect the present invention also provides a method for diagnosing allergies and other conditions associated with excess IgE production in a human which comprises
a) contacting a sample of a biological fluid with an antibody of the present invention, and
b) assaying for the occurrence of binding between said antibody and human IL-4. In the following Examples all temperatures are in degrees Celsius (° C.) and are uncorrected.

The following abbreviations are used:
FACS buffer PBS, 2% FCS and 0.2% $NaN_3$
FCS fetal calf serum
FITC fluoroescein isothiocyanat
$IC_{50}$ inhibitory concentration
KLH keyhole limpet hemocyanin
mAb monoclonal antibody
MTX methotrexate
PBS phosphate buffered saline
sIgD surface Immunoglobulin D
rmIL-3 recombinant murine interleukin-3
rhIL-4 recombinant human interleukin-4
rhIL-13 recombinant human interleukin-13
rpm revolutions per minute
RPMI Roswell Park Memorial Institute medium
RT room temperature
TF-buffer 272 mM sucrose, 1 mM $MgCl_2$, 7 mM phosphate buffer pH 7.4

EXAMPLES

Example 1 a) Antibody Production

Plasmids encoding the variable regions of the sequence SEQ ID NO: 5 or 7 (=heavy chain) and the sequence SEQ ID NO: 6 or 8 (=light chain) of the antibody are cloned into expression cassettes for human kappa light chains and human IgG1 heavy chains. The specificity determining regions are combined with the necessary elements to generate complete monoclonal antibodies, i.e. promoter, leader sequence and splice donor sites for splicing to the antibody constant region exons that are required for the expression of functional immunoglobulin proteins. The variable region cassettes for the heavy and light chain antibodies, encoding for leader sequences, variable region and 3'-prime splice donor sites for splicing the constant region exons CH1-CH4 and kappa, are transferred into mammalian expression vectors HC (heavy chain vector, human IgG1) and LC (light chain vector, human kappa). The light chain containing plasmid and the heavy chain containing plasmid are introduced into Sp2/0 cells in a co-transfection approach. E.g. for transfection, cells in exponential growth phase with a viability of about 95% are used. Cells are washed twice with cold TF-buffer and cell concentration is adjusted to $2 \times 10^7$ cells/ml in TF-buffer. 0.8 ml cell suspension obtained are mixed with 15 µg each of the heavy chain and light chain plasmid and placed on ice for 10 minutes. Transfection is done by electroporation using the Biorad Gene Pulser (280 V and 25 µF). After electroporation, cells are placed on ice for 15 minutes, transferred into 50 ml cold culture medium and incubated for 1 day at 370 and 5% $CO_2$. For clonal amplification, the G418 resistant cells obtained are cultivated in the presence of 200 nM MTX. An aliquot of the heterogeneous cell pool is seeded into 96-well plates at clonal density of 1 viable cell/well in culture medium containing 200 nM MTX allowing selection of clonal populations of amplified cells. Limiting dilution cloning is applied to generate clonal cell lines after amplification and adaptation to serum-free culture conditions. Cells are seeded into two 96-well plates at a concentration of 0.5 cell/well. Wells are screened microscopically for clonality one day after seeding. Only monoclonal antibodies are used for further testing.

The antibody obtained comprises an amino acid sequence of SEQ ID NO:1 and SEQ ID NO:2.

b) Affinity Measurements

Affinity measurements of human mAbs of the present invention are carried on a BIAcore™ 2000 instrument. Anti-human IgG is coated onto a BIAcore sensorchip CM-5 (BIAcore), so that application of defined amounts of human mAbs results in capturing on this prepared surface and hence in a change of refractory properties that are measured. A subsequent application of rhIL4 results in a further change of the refractory properties, which allows determination of the association rate ($K_{on}$, on rate) as well as the dissociation rate ($K_{off}$, off rate) and the product of these two, the affinity ($K_d$, dissociation constant, given in pM), according to the BIAevaluation 3.0 software. Using several concentrations of rhIL4 in BIAbuffer, an affinity of 43 pM of an mAb as defined by CDRs as described in claim 2a) is determined.

c) Determination of Inhibitory Potential on IL-4 Mediated IgE c1) Cell Sources Human B cells are isolated from peripheral blood, respectively, buffy coats by Ficoll-paque density centrifugation, followed by magnetic separation with MACS beads (Miltenyi Biotech) specific for human CD19 or human CD22 on an AutoMACS device.

Naïve human B cells are similarly isolated using anti-human sIgD FITC labeled goat F(ab')$_2$ antibodies followed by anti-FITC MACS beads.

c2) Cell Culture/Maintenance

Transfectants (BaF/3 transfectants carrying the IL-4Rα and the IL-13Rα1) are cultured in RPMI 1640 medium supplemented with Glutamax (Invitrogen), 10% FCS, 1% penicillin/streptomycin and 10 ng/ml rhIL-4 (Novartis). Cells are split 1:1 twice weekly, washed with fresh medium without rhIL-4 and kept in such medium overnight (=starved cells).

Human ex vivo (naïve) B cell cultures are incubated in X-Vivo medium (Cambrex, XV15) supplemented with Glutamax, 10% FCS, 1% penicillin/streptomycin in 96-well plates (Costar).

c3) BAF Cell Proliferation Assay

Starved cells as described in b) are collected, washed with fresh medium, counted and adjusted to 2×105 cells/ml of which 100 µl per well are distributed to 96-well plates (Costar). For titration series the cytokines rhIL-4, rhIL-13 and rmIL-3 are prepared in 4 times the desired final concentration in the same medium.

For titration series antibodies are either used as cell culture supernatants with ELISA determined concentrations or from purified material at 4 times the desired concentrations in the same medium. The pre-dilutions of cytokines and antibodies are mixed at equal volumes and 100 µl of the pre-mix are transferred to the well prepared with cells. Controls are set up for background proliferation (medium without cytokine and without antibody=100% inhibition) and maximum proliferation (medium with cytokine only=0% inhibition).

After overnight incubation at 370 in the presence of 5% $CO_2$, [methyl-3H]thimidine (Amersham TRK120) 1 µCi per well is added in 10 µl of medium and incubated for 8 hours. Following a freeze/thaw cycle cells are harvested from the plates on filter mats using a Tomtek harvester. Filter mats are dried in a microwave oven for 2 minutes at 650 W and transferred to a sample bag together with a sheet of Meltilex Scintillation Wax (Wallac). Wax is melted through the filter and filters obtained are placed inside appropriate cassettes and inserted into a micro-beta reader (Wallac) for scintillation counting using a program measuring 30 seconds per field and extrapolating to counts per minutes.

An $IC_{50}$ of 30 pM is measured in this test system for the antibody.

c4) IL-4 Induced CD23 Up-Regulation on B Cells

MACS separated B cells are adjusted to 0.5-1×106 cells/ml in XV15 and plated out in 100 µl per well of 96 well round bottom plates. Cytokines (1 ng/ml final) and mAb (2 µg/ml-2 ng/ml final) are pre-diluted and pre-mixed as described above and added in 100 µl to reach a final volume of 200 µl.

After culturing overnight at 37° in the presence of 5% $CO_2$ cells are transferred to 96-well plates (Costar) and centrifuged at 2200 rpm (~1000×g) for 1 minute after flicking off the supernatant washed with FACS buffer.

Florochrome labeled mAbs [HLA-DR FITC (Caltag#MHLDR01 1:800), CD19 PE (Caltag#MHCD1904 1:200) and CD23 APC (Caltag#MHCD2305 1:200)] are prepared in FACS buffer and distributed in 50 µl per well. After 30-60 minutes incubation at RT, wells are filled up with FACS buffer, centrifuged and the centrifugation residue obtained is washed with FACS buffer. Cells are re-suspended in FACS buffer with 2 µg/ml propidium iodide and analyzed on a dual laser FacsCalibur flow cytometer (BD Biosciences). Cells are gated according to their forward scatter and side scatter properties as well as their ability to exclude propidium iodide and their CD19 expression. Mean fluorescence intensities and percentage of cells above arbitrary threshold (set on un-induced cells) in CD23 expression are determined. Baseline expression (100% inhibition) is determined on cells without cytokine, whereas 0% inhibition is set on cells incubated with cytokine but without mAb.

An $IC_{50}$ of 334 pM for this antibody is determined for IL-4 induced CD23 expression on the cells as described above in the presence of 70 pM recombinant human IL-4.

c5) IL4 Induced IgE Production by Naïve B Cells

Magnetically sorted naïve B cells are adjusted to 3×105 cells per ml in XV15 and plated out in 100 µl per well of 96-well plates in a 6×6 array in the center of the plate, surrounded by PBS filled wells during the 10 days of culture at 37° in the presence of 5% $CO_2$. One plate each is prepared per mAb to be tested, consisting of 3 wells each un-induced and induced controls and quintuplicate repeats of mAb titrations starting at 7 µg/ml and running in 3-fold dilution down to 29 ng/ml final concentrations added in 50 µl four times concentrated pre-dilution. Inducing conditions are rhIL-4 at 20 ng/ml plus anti-CD40 mAb (Novartis) at 0.5 µg/ml final concentrations also added in 50 µl of four times concentrated pre-dilution. IgE concentrations are determined at the end of the culture period by a standard sandwich ELISA method.

An $IC_{50}$ of 2806 pM for this antibody is determined for IL-4 induced IgE on the cells as described above.

Examples 2 to 6

Antibodies are obtained analogously as described in example 1 and comprise the following amino acid sequences:

Example 2 is an antibody comprising amino acid sequence SEQ ID NO:9 and SEQ ID NO:10.

Example 3 is an antibody comprising amino acid sequence SEQ ID NO:17 and SEQ ID NO:18.

Example 4 is an antibody comprising amino acid sequence SEQ ID NO:25 and SEQ ID NO:26.

Example 5 is an antibody comprising amino acid sequence SEQ ID NO:33 and SEQ ID NO:34.

Example 6 is an antibody comprising amino acid sequence SEQ ID NO:41 and SEQ ID NO:42.

Table 1 summarizes the $IC_{50}$ values of the antibodies in the various test systems as described in Example 1b to c.

TABLE 1

| | $K_d$ [pM] | IC50 [pM] measured in the particular assays | | |
| --- | --- | --- | --- | --- |
| | | BAF cell proliferation | IL-4 induced CD23 | IL-4 induced IgE |
| Ex. 1 | 43 | 30 | 334 | 2806 |
| Ex. 2 | 59 | 50 | 463 | 5339 |
| Ex. 3 | 89 | 84 | 873 | 7813 |
| Ex. 4 | 66 | 688 | 848 | 7570 |
| Ex. 5 | 84 | 218 | 2835 | 9944 |
| Ex. 6 | 170 | 167 | 2869 | 2648 |

The invention claimed is:

1. An antibody comprising a heavy chain polypeptide comprising the amino acid sequence of SEQ ID NO:1 and a light chain polypeptide comprising the amino acid sequence of SEQ ID NO:2.

2. An antibody comprising a heavy chain polypeptide comprising the amino acid sequence of SEQ ID NO:3 and a light chain polypeptide comprising the amino acid sequence of SEQ ID NO:4.

3. The antibody of claim 1 or 2 that is monoclonal.

4. A pharmaceutical composition comprising an antibody of claim 1 or 2 in association with at least one pharmaceutically acceptable excipient.

* * * * *